United States Patent [19]

Quallich et al.

[11] Patent Number: 4,777,288

[45] Date of Patent: Oct. 11, 1988

[54] PROCESS FOR PREPARING A 4,4-DIPHENYLBUTANOIC ACID DERIVATIVE

[75] Inventors: George J. Quallich, North Stonington, Conn.; Michael T. Williams, Deal, England

[73] Assignee: Pfizer Inc., New Yok, N.Y.

[21] Appl. No.: 60,577

[22] Filed: Jun. 11, 1987

[51] Int. Cl.[4] .................... C07C 63/33; C07D 307/26
[52] U.S. Cl. .................... 562/491; 549/324; 562/470
[58] Field of Search ............... 562/491, 470; 549/324

[56] References Cited

U.S. PATENT DOCUMENTS 4,536,518 8/1985 Welch, Jr. et al. ................ 514/647

FOREIGN PATENT DOCUMENTS 0028901 5/1981 European Pat. Off. ........... 562/491
0030081 6/1981 European Pat. Off. ........... 562/491

OTHER PUBLICATIONS

Boger, D. L. et al., Tetrahedron Letters vol. 25, No. 49, pp. 5615–18, 1984.
Chemical Abstract 106 (13) 101813e Rao C et al. Indian J. Chem. Sec B 25B (6) 626–629, 1986.
R. V. Christian, Jr., "Condensation of Lactones with Benzene," Journal of Organic Chemistry, vol. 74, p. 1591 (1952).
W. M. Welch, Jr. et al., Journal of Medicinal Chemistry, vol. 27, No. 11, p. 1508 (1984).
E. A. Stech et al., Journal of the American Chemical Society, vol. 75, p. 1117 (1953).

*Primary Examiner*—Paul J. Killos
*Attorney, Agent, or Firm*—Peter C. Richardson; Lawrence C. Akers

[57] ABSTRACT

A novel three-step process for preparing 4-(3,4-dichlorophenyl)-4-phenylbutanoic acid is disclosed, which involves (1) reducing 4-(3,4-dichlorophenyl)-4-ketobutanoic acid to 4-(3,4-dichlorophenyl)-4-hydroxybutanoic acid; (2) then converting the intermediate hydroxy acid formed in the first step to 5-(3,4-dichlorophenyl)-dihydro-2(3H)-furanone, and (3) thereafter reacting the resulting gamma-butyrolactone compound with benzene in a Friedel-Crafts type reaction to form the desired final product. The latter compound is known to be useful as an intermediate leading to cis-(1S)(4S)- -N-methyl-4-(3,4-dichlorophenyl)-1,2,3,4-tetrahydro-1-naphthaleneamine (sertraline), which is known to be a preferred anti-depressant agent in the field of medicinal chemistry. The aforementioned 5-(3,4-dichlorophenyl)-dihydro-2(3H)-furanone and 4-(3,4-dichlorophenyl)-4-hydroxybutanoic acid are both novel compounds.

22 Claims, No Drawings

PROCESS FOR PREPARING A 4,4-DIPHENYLBUTANOIC ACID DERIVATIVE

BACKGROUND OF THE INVENTION

This invention relates to a new and useful process for preparing a known 4,4-diphenylbutanoic acid derivative. More particularly, it is concerned with a novel three-step process for preparing 4-(3,4-dichlorophenyl)-4-phenylbutanoic acid, which serves as a key intermediate in the production of the antidepressant agent known as cis-(1S) (4S)-N-methyl-4-(3,4-dichlorophenyl)-1,2,3,4-tetrahydro-1-naphthaleneamine (sertraline). The invention also includes within its scope such novel compounds as 4-(3,4-dichlorophenyl)-4-hydroxybutanoic acid and 5-(3,4-dichlorophenyl)-dihydro-2(3H)-furanone, which are used as intermediates in the aforesaid three-step novel process.

In accordance with the prior art, there is described in U.S. Pat. No. 4,536,518 to W. M. Welch, Jr. et al., as well as in the paper of W. M. Welch, Jr. et al. appearing in the *Journal of Medicinal Chemistry*, Vol. 27, No. 11, p. 1508 (1984), a method for preparing certain 4-(substituted phenyl)-4-(optionally-substituted phenyl)-butanoic acids wherein the optional substituent is always other than alkoxy. These particular 4,4-diphenylbutanoic acid derivatives are shown to be useful as intermediates that lead to various anti-depressant derivatives of cis-4-phenyl-1,2,3,4-tetrahydro-1-naphthaleneamine, including cis-(1S) (4S)-N-methyl-4-(3,4-dichlorophenyl)-1, 2,3,4-tetrahydronaphthaleneamine (sertraline) which is an especially preferred embodiment in this series. The prior art method disclosed in the aforesaid publications of W. M. Welch, Jr. et al. involves synthesizing the desired 4,4-diphenylbutanoic acid intermediates in a plurality of steps starting from the corresponding benzophenone compound. For instance, the appropriately substituted benzophenone starting material is first subjected to a base-catalyzed Stobbe condensation with diethyl succinate, followed by hydrolysis and decarboxylation with 48% aqueous hydrobromic acid to yield the corresponding 4,4-diphenylbut-3-enoic acid, which is thereafter reduced by catalytic hydrogenation or by the use of hydriodic acid and red phosphorus to finally yield the desired 4,4-diphenylbutanoic acid intermediate.

SUMMARY OF THE INVENTION

In accordance with the present invention, there is now provided a new and improved process for preparing 4-(3,4-dichlorophenyl)-4-phenylbutanoic acid, known to be useful as an intermediate as hereinbefore discussed, by a novel three-step method starting from 4-(3,4-dichlorophenyl)-4-ketobutanoic acid whereby the desired final product is readily obtained in pure form and in high yield. More particularly, the novel three-step method of the invention is directed to a process for preparing a compound of the formula:

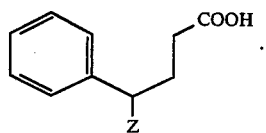

wherein Z is 3,4-dichlorophenyl, i.e., the compound known as 4-(3,4-dichlorophenyl)-4-phenylbutanoic acid, which comprises the steps of:

(a) subjecting 4-(3,4-dichlorophenyl)-4-ketobutanoic acid of the formula:

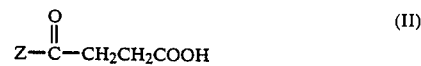

wherein Z is as previously defined, to the selective action of a carbonyl reducing agent in a polar protic solvent or an aprotic solvent at a temperature of from about 0° C. to about 100° C. until the reduction reaction to form the desired 4-(3,4-dichlorophenyl)-4-hydroxybutanoic acid intermediate is substantially complete:

(b) converting the intermediate hydroxy acid formed in step (a) to the corresponding dihydro-2(3H)-furanone compound of the formula:

wherein Z is as previously defined; and (c) thereafter reacting the resulting gammabutyrolactone compound formed in step (b) with benzene in an excess of said reagent as solvent or in a reaction-inert organic solvent in the presence of a Friedel-Crafts type catalyst at a temperature of from about 0° C. to 100° C. until the alkylation of benzene by the aforesaid gammalactone compound of formula (III) to form the desired final product of formula (I) is substantially complete.

In this way, a compound such as 4-(3,4-dichlorophenyl)-4-ketobutanoic acid is readily converted, via the novel intermediates 4-(3,4-dichlorophenyl)-4-hydroxybutanoic acid and 5-(3,4-dichlorophenyl)-dihydro-2(3H)-furanone, respectively, to 4-(3,4-dichlorophenyl)-4-phenylbutanoic acid in a most facile manner. As previously indicated, the latter-named final product is known to be useful as a valuable intermediate in the production of the antidepressant agent sertraline, which is cis-(1S) (4S)-N-methyl-4-(3,4-dichlorophenyl)-1,2,3,4-tetrahydro-1-naphthaleneamine [see U.S. Pat. No. 4,536,518 as well as *Journal of Medicinal Chemistry*, Vol. 27, No. 11, p. 1508 (1984)].

Accordingly, there is also included within the purview of this invention the novel gamma-butyrolactone compound produced in step (b), which is useful as an intermediate for the production of the final product hereinbefore described. The present invention therefore includes the novel 5-(substituted phenyl)-dihydro-2(3H)-furanone compound of the formula:

wherein Z is 3,4-dichlorophenyl, i.e., the compound designated as 5-(3,4-dichlorophenyl)-dihydro-2(3H)-furanone. This particular 5-(substituted phenyl)-dihydro-2(3H)-furanone is the intermediate that specifically leads to 4-(3,4-dichlorophenyl)-4-phenylbutanoic acid and ultimately, to sertraline as previously discussed.

Additionally, the invention also includes within its purview the novel compound designated as 4-(3,4- dichlorophenyl)-4-hydroxybutanoic acid, which is used as a starting material in step (b) to produce the aforesaid novel gamma-butyrolactone intermediate per se. Accordingly, the present invention also includes the novel hydroxy acid compound of the formula:

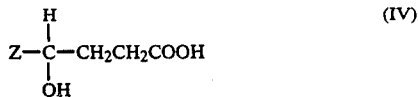

and its alkali metal and amine addition salts, wherein Z is 3,4-dichlorophenyl. This particular acid is the key starting material in step (b) that serves as a useful intermediate in the synthesis which ultimately leads to sertraline.

DETAILED DESCRIPTION OF THE INVENTION

In accordance with the process of this invention, the reduction of 4-(3,4-dichlorophenyl)-4-ketobutanoic acid to 4-(3,4-dichlorophenyl)-4-hydroxybutanoic acid in step (a) is accomplished by using a carbonyl reducing agent that is capable of reducing a ketone in the presence of a carboxylic acid or a salt thereof. This category includes alkali metal borohydrides and related reagents, amineboranes and lithium aluminum hydride derived reagents and dialkylaluminum hydride reagents. In general, the reduction step is carried out in a polar protic or an aprotic solvent at a temperature of from about 0° C. to about 100° C. until the reduction reaction to form the desired 4-hydroxy compound is substantially complete. Preferred polar protic solvents for use in this connection include water and lower alkanols ($C_1$–$C_4$) such as methanol, ethanol and isopropanol, etc., while preferred aprotic solvents include acetonitrile, dimethylformamide, diethylformamide, dimethylacetamide, dioxane, tetrahydrofuran, benzene and the like. The latter type solvents are especially preferred when using reagents other than the alkali metal borohydrides. A preferred embodiment involves the use of an alkali metal borohydride, such as sodium borohydride and the like, in a polar protic solvent, such as water, at a temperature of from about 50° C. to about 75° C. The pH for the reaction in this type solvent medium will normally range from about pH 6 to about pH 12. In practice, the starting keto-acid is dissolved in water containing a sufficient amount of an alkali metal hydroxide to maintain the pH within the aforesaid desired range. Upon completion of the reaction, the desired 4-(3,4-dichlorophenyl)-4-hydroxybutanoic acid intermediate is readily recovered from the reaction mixture in accordance with conventional procedure or used as such (i.e., in situ) in the next reaction step without any further treatment being necessary. When the reaction is conducted in an aqueous alkaline solvent medium as described above (pH>6), the hydroxy acid final product will normally be present in the form of an alkali metal salt.

The intermediate hydroxy acid formed in step (a) is then converted to the corresponding gamma-butyrolactone compound of structural formula (III) by first isolating the hydroxy acid from the reaction mixture as indicated above and thereafter heating said acid in an aromatic hydrocarbon solvent at a temperature that is in the range of from about 55° C. to about 150° C. until the conversion to the aforesaid lactone compound is substantially complete. Preferred aromatic hydrocarbon solvents for these purposes include those having from six to eight carbon atoms such as benzene, toluene, xylene, and the like. benzene is especially preferred in this connection as the reaction mixture can then be used directly in the next reaction step, i.e., the Friedel-Crafts type alkylation of step (c) without any isolation of the intermediate lactone compound being necessary.

Alternatively, the conversion of 4-(3,4-dichlorophenyl)-4-hydroxybutanoic acid which is formed in step (a) to the corresponding gamma-butyrolactone compound formed in step (b) is effected by heating the hydroxy acid in situ in an aqueous acid solvent medium at a temperature of from about 20° C. to about 100° C. until the conversion to the lactone compound of structural formula (III) is substantially complete. The aqueous acid solvent medium is preferably obtained by acidifying the warm aqueous alkaline solvent medium obtained in step (a); the latter medium also contains the intermediate hydroxy acid starting material of structural formula (IV) that had previously been formed in situ. The preferred acid for purposes of acidification in this connection is either hydrochloric acid or sulfuric acid, and the heating step (b) is preferably conducted at a temperature of from about 55° C. to about 80° C. until lactonization is substantially complete. Upon completion of this step, the final reaction mixture is slowly cooled to ambient temperatures and granulated in a conventional manner, while the desired 5-(3,4-dichlorophenyl)-dihydro-2 (3H)-furanone compound is thereafter preferably isolated from the mixture by using such means as suction filtration and the like, or else by means of extraction with a solvent, such as methylene chloride, which is also suitable for the next step.

The third and final stage of the multi-step process of the present invention involves reacting the gamma-lactone compound obtained in step (b) with benzene in an excess of said reagent as solvent or in a reaction-inert organic solvent in the presence of a Friedel-Crafts type catalyst at a temperature of from about 0° C. to about 100° C. until the alkylation of benzene by the gamma-lactone compound of formula (III) to form the desired final product of formula (I) is substantially complete. Preferred reaction-inert organic solvents for use in this particular alkylation step include carbon disulfide, nitrobenzene, various lower nitroalkanes like nitromethane and nitroethane, as well as halogenated benzene compounds such as o-dichlorobenzene and bromobenzene, in addition to various halogenated lower hydrocarbon solvents such as methylene chloride, ethylene dichloride, chloroform, trichloroethylene, s-tetrachloroethane and carbon tetrachloride, etc. The preferred Friedel-Crafts type catalyst for the reaction of step (c) is aluminum chloride. In a preferred embodiment of this particular step, the molar ratio of the gamma-butyrolactone compound of structural formula (III) employed as starting material in said step to the benzene reagent and the aluminum chloride catalyst is in the range of from about 1.0:1.0 to about 1.0:20.0 and from about 1.0:0.5 to about 1.0:10.0, respectively, with the preferred range that is directed to the optimum ratio being between about 1.0:2.0 and about 1.0:15.0 (gamma-butyrolactone/benzene) and between about 1.0:1.0 and about 1.0:2.0 (gamma-butyrolactone/aluminum chloride), respectively. Thus, for example, a most preferred optimum ratio has been found to about 1.0:2.5 in the case of gamma-butyrolactone/benzene and about 1.0:1.0 when dealing with the gamma-butyrolactone/aluminum chloride component. It is to be understood, of course, that the amount of benzene employed will be dependent upon whether it is also used as a solvent for the reaction or merely as a reagent in conjunction with another inert organic solvent of the type previously discussed (e.g., methylene chloride). The most preferred solvents for these purposes are therefore either benzene or a halogenated lower hydrocarbon solvent like methylene chloride, with the Friedel-Crafts alkylation reaction of step (c) being preferably conducted at a temperature of from about 10° C. to about 30° C. Upon completion of this step, the desired 4-(3,4-dichlorophenyl)-4-phenylbutanoic acid is readily recovered from the reaction mixture in a conventional manner common to Friedel-Crafts type reactions, viz., by first pouring the mixture onto stirred ice containing a mineral acid such as concentrated hydrochloric acid, followed by further stirring to effect a separation of the phases and subsequent isolation of the product from the organic phase, with the latter step being preferably accomplished by evaporation of the solvent therefrom and crystallization of the resulting resulting residue, etc. In this way, the novel three-step process of this invention to prepare the valuable 4-(3,4-dichlorophenyl)-4-phenylbutanoic acid from 4-(3,4-dichlorophenyl)-4-ketobutanoic acid is now complete.

The 4-(3,4-dichlorophenyl)-4-ketobutanoic acid starting material required for conducting the process of this invention is a known compound which can easily be synthesized by those skilled in the art starting from common chemical reagents and using conventional methods of organic synthesis. For instance, this particular compound is readily prepared by employing the method of E. A. Steck et al., as described in the *Journal of the American Chemical Society*, Vol. 75, p. 1117 (1953).

As previously indicated, the 4-(3,4-dichlorophenyl)-4-phenylbutanoic acid final product afforded by the process of this invention is a valuable intermediate that ultimately leads to the antidepressant agent known as sertraline or cis-(1S) (4S)-N-methyl-4-(3,4-dichlorophenyl)-1, 2,3,4-tetrahydro-1-naphthaleneamine as disclosed in the previously discussed prior art. More specifically, 4-(3,4-dichlorophenyl)-4-phenylbutanoic acid is first converted to 4-(3,4-dichlorophenyl)-3, 4-dihydro-1-(2H)-naphthalenone and then finally to racemic cis-N-methyl-4-(3,4-dichlorophenyl)-1, 2,3,4-tetrahydro-1-naphthaleneamine prior to ultimately yielding the desired cis-(1S) (4S)-N-methyl-4-(3,4-dichlorophenyl)-1, 2,3,4-tetrahydro-1-naphthaleneamine by the multistep method of the prior art process as earlier described by W.M. Welch, Jr. et al. in U.S. Pat. No. 4,536,518 and the *Journal of Medicinal Chemistry*, Vol. 27, No. 11, p. 1508 (1984).

Hence, the novel process of the present invention now provides the required and valuable 4-(3,4-dichlorophenyl)-4-phenylbutanoic acid discussed above in pure form and in high yield by a unique three-step method, which represents a major improvement in view of the ease of synthesis and greatly reduced nature of the costs involved.

EXAMPLE 1

A 193 g. (0.781 mole) sample of 4-(3,4-dichlorophenyl)-4-ketobutanoic acid [E. A. Steck et al., *Journal of the American Chemical Society*, Vol. 75, p. 1117 (1953)] was slurried with 772 ml. of water in a reaction flask and heated to 70°-80° C., while 70 ml. of 15N aqueous sodium hydroxide (1.05 mole) were slowly added thereto over a period of one-half hour with the system being maintained within the pH range of 10.7-11.9. The pH value of the resulting dark brown solution was pH 11.7 (at 75° C.), at which point a solution consisting of 10.35 g. (0.272 mole) of sodium borohydride dissolved in 52.2 ml. of water containing 0.53 ml. of 15N aqueous sodium hydroxide (0.008 mole) was added thereto during the course of a one-half hour period. Upon completion of this step, the resulting reaction mixture was further stirred at this same temperature for a period of 45 minutes. Thin layer chromatography (T.L.C) analysis of a sample taken at this point showed the complete absence of the keto-acid starting material. This solution now contained 4-(3,4-dichlorophenyl)-4-hydroxybutanoic acid in the form of the sodium salt.

A 50 ml. aliquot of the above alkaline solution (5% by volume) was then removed from the reaction flask and ice-cooled to 0°-10° C., while the pH was adjusted to pH 1.0 by the addition of 5N hydrochloric acid (with the temperature always being maintained below 10° C. throughout the course of this addition step). Upon completion of this step, the resulting solution was extracted with methylene chloride and the organic extracts were thereafter combined, washed with water and dried over anydrous sodium sulfate. After removal of the drying agent by means of filtration and the solvent by means of evaporation under reduced pressure, there were obtained 10 g. of 4-(3,4-dichlorophenyl)-4-hydroxybutanoic acid in the form of a brown-orange residual oil. The latter material was subsequently dissolved in 40 ml. of diethyl ether and to this solution there was added, in one portion, a solution consisting of 9.05 g. (0.05 mole) of dicyclohexylamine dissolved in 30 ml. of diethyl ether. The resulting crystalline slurry was then stirred and cooled to 10° C. for a period of one hour. In this way, there was readily obtained the corresponding crystalline dicyclohexylamine salt, which was thereafter recovered by means of suction filtration, washed with diethyl ether and dried in vacuo to constant weight to ultimately afford 9.6 g. of pure 4-(3,4-dichlorophenyl)-4-hydroxybutanoic acid (as the dicyclohexylamine salt), m.p. 152°-154° C. Recrystallization of the latter material (9.4 g.) from ethyl acetate (300 ml.) did not raise the melting point.

EXAMPLE 2

A mixture consisting of 370.62 g. (1.5 moles) of 4-(3,4-dichlorophenyl)-4-ketobutanoic acid [E. A. Steck et al., *Journal of the American Chemical Society*, Vol. 75, p. 1117 (1953)] and 1.505 liters of demineralized water was stirred and heated at 70°-80° C., while 130 ml. of 15N aqueous sodium hydroxide and 47.5 ml. of 1.5N aqueous sodium hydroxide were gradually added thereto in aliquot portions. The total time required for obtaining complete solution was approximately one hour, with the pH value of the resulting dark brown solution being pH 10.73 (at 78° C). This solution was then transferred to a 5-liter flange flask and the temperature was maintained at ca. 65° C. (±3° C.), while a solution consisting of 19.86 g. (0.525 mole) of sodium borohydride dissolved in 100.3 ml. of demineralized water containing 1.03 ml. of 15N aqueous sodium hydroxide was added dropwise thereto during the course of a 44-minute period. Upon completion of this step, the resulting reaction mixture was further stirred at this same temperature for a period of approximately two hours. Thin layer chromatography (T.L.C.) analysis of a sample taken six minutes after completion of the addition step showed the complete absence of the keto-acid starting material. This solution now contained 4-(3,4-dichlorophenyl)-4-hydroxybutanoic acid in the form of the sodium salt. It was used as such (viz., in situ) in the next step of the process without any isolation of the product being necessary.

EXAMPLE 3

The warm aqueous alkaline solution containing 4-(3,4-dichlorophenyl)-4-hydroxybutanoic acid, as described in Example 2, was stirred and heated at 57°–62° C., while 5.8N hydrochloric acid (436 ml.) was slowly added dropwise thereto during the course of a 65-minute period with particular care being taken during the first one-half hour of the addition step due to the formation of a foam. Upon completion of this step, the resulting reaction mixture of oil and acidified water was vigorously stirred and heated at 65°–70° C. for a period of four hours prior to being allowed to cool to room temperature (ca. 20° C.). Thin layer chromatography (T.L.C.) analysis of samples taken from the mixture at 1, 2, 2.5 and 3.5 hours after start of the final heating step showed that conversion of the hydroxy acid to the lactone was complete after 3.5 hours. The final mixture was allowed to gradually cool and granulate overnight for a period of approximately 16 hours, and the white-colored solid precipitate thus obtained was subsequently recovered by means of suction filtration and thereafter washed with two-80 ml. portions of demineralized water. After first air-drying on the filter funnel and then drying in vacuo at 46° C. in a vacuum over overnight (ca. 16 hours), there were finally obtained 320 g. (92%) of pure 5-(3,4-dichlorophenyl)-dihydro-2(3H)-furanone, m.p. 64°–65° C.

EXAMPLE 4

To a well-stirred slurry consisting of 19.5 g. (0.25 mole) of benzene and 13.5 g. (0.10 mole) of aluminum chloride in 22.5 ml. of methylene chloride, there was added in a dropwise manner a solution consisting of 23.1 g. (0.10 mole) of 5-(3,4-dichlorophenyl)-dihydro-2(3H)-furanone (the product of Example 3) dissolved in 22.5 ml. of methylene chloride. The addition step was carried out during the course of a 15-minute period, during which time the temperature of the reaction mixture rose from 23° C. to 35° C. Upon completion of this step, the reaction mixture was stirred at room temperature (ca. 20° C.) for a period of two hours, during which time a dark brown solution resulted. Thin layer chromatography (T.L.C.) analysis of a sample of the mixture taken at the 1.5-hour mark revealed no starting material to be present at this point. The stirred mixture was next poured onto 100 g. of ice containing 20 ml. of concentrated hydrochloric acid, and the resulting aqueous acidic mixture was stirred for a period of 15 minutes. The organic phase of the resulting two-phase system was then separated and washed well with water, followed by atmospheric distillation to remove the methylene chloride. The residual liquid was then treated with hexane in a dropwise manner and allowed to cool to room temperature, which resulted in the precipitation of a light brown solid. The latter material was granulated at room temperature for a period of one hour, and finally recovered from the mixture by means of suction filtration and washed with a small portion of fresh hexane. After drying in vacuo to constant weight, there were ultimately obtained 28.0 g. (91%) of 4-(3,4-dichlorophenyl)-4-phenylbutanoic acid, m.p. 121°–122° C. [literature m.p. 118°–120° C., according to W. M. Welch, Jr. et al. in either U.S. Pat. No. 4,536,518 or *Journal of Medicinal Chemistry*, Vol. 27, No. 11, p. 1508 (1984)]. A nuclear magnetic resonance spectrum of the material was found to be identical with that of an authentic sample prepared by the procedure described by W. M. Welch, Jr. et al. in the aforesaid prior art.

EXAMPLE 5

To a well-stirred slurry consisting of 126.4 g. (1.49 moles) of benzene and 86.4 g. (0.640 mole) of aluminum chloride contained in a 2-liter four-necked, round-bottomed reaction flask under a nitrogen atmosphere at 18° C., there was slowly added in a dropwise manner a solution consisting of 149.6 g (0.648 mole) of 5-(3,4-dichlorophenyl)-dihydro-2(3H)-furanone (the product of Example 3) dissolved in 800 ml. of benzene. The addition step was carried out during the course 50-minute period, during which time the temperature of the reaction mixture was maintained in the range of ca. 15°–20° C. with the aid of an ice bath. Upon completion of the step, the reaction mixture was stirred at room temperature (ca. 20° C.) for a period of two hours, during which time a brown solution resulted. The stirred mixture was next poured into 648 ml. of ice/water containing 129.6 ml. of concentrated hydrochloric acid at 1° C., and the resulting aqueous acidic mixture was stirred for a period of one-half hour. The organic phase of the resulting two-phase system was then separated from the aqueous phase, and the latter was saved and twice extracted with 100 ml. of benzene. The combined benzene layers were then filtered and thereafter subjected to vacuum distillation to remove the benzene. The off-white, golden tan solid residue which remained was then granulated with 500 ml. of hexanes for a period of 45 minutes, filtered and subsequently washed with three-100 ml. portions of fresh hexanes. The solid product and the hexane washes were then transfered to a 2000 ml. three-necked, round-bottomed flask and granulated for a period of approximately 16 hours. After filtering and washing the recovered product with another three-100 ml. portions of fresh hexanes, followed by vacuum drying at ca. 50° C., there were finally obtained 154.7 g. (77%) of pure 4-(3,4-dichlorophenyl)-4-phenylbutanoic acid in the form of an off-white solid powder. This product was identical in every respect with the product of Example 4.

EXAMPLE 6

To a well-stirred slurry consisting of 126.22 g. 1.49 moles) of benzene (146.3 ml.) and 86.4 g. of (0.640 mole) of aluminum chloride in 186 ml. of o-dichlorobenzene contained in a 2-liter four-necked, round-bottom reaction flask under a nitrogen atmosphere at 7° C., there was slowly added in a dropwise manner a solution consisting of 149.6 g. (0.648 mole) of 5-(3,4-dichlorophenyl)-dihydro-2(3H)-furanone (the product of Example 3) dissolved in 600 ml. of o-dichlorobenzene. The addition step was carried out during the course of a 2.5-hour period, during which time the temperature of the reaction mixture was maintained in the range of ca. 7°–9° C. with the aid of an ice bath. Upon completion of this step, the reaction mixture was stirred at room temperature (ca. 20° C.) for a period of 35 minutes and then quenched into a mixture of 650 ml. of water and 130 ml. of concentrated hydrochloric acid at −4° C., with the temperature of the resulting aqueous acidic mixture always being maintained below 28° C. throughout the course of the quenching step. The latter mixture (now a white slurry) was stirred for a period of ten minutes and then allowed to separate into two layers. The saved organic layer was washed twice with an equal volume of warm water, and a 550 ml. aliquot of this washed layer was then transferred into a 3-liter four-necked, round-bottomed flask and charged with 500 ml. of water and 60 ml. of 50% aqueous sodium hydroxide solution, followed by stirring for a period of ten minutes. The resulting organic layer was then separated from the aqueous caustic layer and re-extracted once again with 500 ml. of 50% aqueous sodium hydroxide. The combined aqueous caustic layers were next extracted with 300 ml. of methylene chloride, and the latter organic layer was thereafter separated, saved and then subjected to vacuum distillation to remove most of the methylene chloride. After seeding the residual thick liquid material with a pinch of authentic 4-(3,4-dichlorophenyl)-4-phenylbutanoic acid (prepared as in Example 4), followed by stirring for a period of approximately one-half hour, there resulted a very thick crystalline slurry which was thereafter charged with 400 ml. of heptane. The resulting mixture was then stirred for a period of approximately 16 hours (i.e., overnight), filtered and the crystalline product subsequently recovered by means of suction filtration and washed with a fresh portion of heptane to afford a white solid material. After repulping the latter product with 500 ml. of hexane, and then filtering and drying same in a vacuum oven to constant weight, there were ultimately obtained 82.0 g. (41%) of pure 4-(3,4-dichlorophenyl)-4-phenylbutanoic acid identical in every respect with the product of Example 4.

What is claimed is:

1. A process for preparing 4-(3,4-dichlorophenyl)-4-phenylbutanoic acid, which comprises the steps of:
   (a) subjecting 4-(3,4-dichlorophenyl)-4-keto-butanoic acid to the selective action of a carbonyl reducing agent in a polar protic or an aprotic solvent at a temperature of from about 0° C. to about 100° C. until the reduction reaction to form the desired 4-(3,4-dichlorophenyl)-4-hydroxybutanoic acid intermediate is substantially complete;
   (b) converting the intermediate hydroxy acid formed in step (a) to 5-(3,4-dichlorophenyl)-dihydro-2(3H)-furanone; and
   (c) thereafter reacting the resulting gamma-butyrolactone compound formed in step (b) with benzene in an excess of said reagent as solvent or in a reaction-inert organic solvent in the presence of a Friedel-Crafts type catalyst at a temperature of from about 0° C. to about 100° C. until the alkylation of benzene by the aforesaid gamma-lactone compound to form the desired 4-(3,4-dichlorophenyl)-4-phenylbutanoic acid is substantially complete.

2. A process as claimed in claim 1 wherein the carbonyl reducing agent employed in step (a) is an alkali metal borohydride.

3. A process as claimed in claim 2 wherein the alkali metal borohydride is sodium borohydride.

4. A process as claimed in claim 2 wherein the polar protic solvent employed in step (a) is water.

5. A process as claimed in claim 4 wherein the reduction reaction in step (a) is conducted at a temperature of from about 50° C. to about 75° C.

6. A process as claimed in claim 1 wherein the conversion of the intermediate 4-(3,4-dichlorophenyl)-4-hydroxybutanoic acid formed in step (a) to 5-(3,4-dichlorophenyl)-dihydro-2(3H)-furanone formed in step (b) is effected by first isolating the hydroxy acid from the reaction mixture and thereafter heating said acid in an aromatic hydrocarbon solvent at a temperature that is in the range of from about 55° C. to about 150° C. until the conversion to the desired gamma-lactone compound is substantially complete.

7. A process as claimed in claim 6 wherein the aromatic hydrocarbon solvent is benzene.

8. A process as claimed in claim 6 wherein the aromatic hydrocarbon solvent is toluene.

9. A process as claimed in claim 1 wherein the conversion of the intermediate 4-(3,4-dichlorophenyl)-4-hydroxybutanoic acid formed in step (a) to 5-(3,4-dichlorophenyl)-2(3H)-furanone formed in step (b) is effected by heating the hydroxy acid in situ in an aqueous acid solvent medium at a temperature from about 20° C. to about 100° C. until the conversion to the desired gamma-lactone compound is substantially complete.

10. A process as claimed in claim 9 wherein the heating step is conducted at a temperature of from about 55° C. to about 80° C. until lactonization is substantially complete.

11. A process as claimed in claim 9 wherein the acid employed in the aqueous acid solvent medium is hydrochloric acid.

12. A process as claimed in claim 9 wherein the acid employed in the aqueous acid solvent medium is sulfuric acid.

13. A process as claimed in claim 1 wherein the Friedel-Crafts type catalyst employed in step (c) is aluminum chloride.

14. A process as claimed in claim 13 wherein the molar ratio of the gamma-butyrolactone compound employed as starting material in step (c) to the benzene reagent and the aluminum chloride catalyst is in the range of from about 1.0:1.0 to about 1.0:20.0 and from about 1.0:0.5 to about 1.0:10.0, respectively.

15. A process as claimed in claim 14 wherein the gamma-butyrolactone/benzene/aluminum chloride molar ratio is about 1.0:15.0:1.0.

16. A process as claimed in claim 14 wherein the gamma-butyrolactone/benzene/aluminum chloride molar ratio is about 1.0:2.0:1.0.

17. A process as claimed in claim 1 wherein the Friedel-Crafts alkylation reaction of step (c) is conducted at a temperature of from about 10° C. to about 30° C.

18. A process as claimed in claim 1 wherein the reaction-inert organic solvent employed in step (c) is methylene chloride.

19. A process as claimed in claim 1 wherein the reaction-inert organic solvent employed in step (c) is o-dichlorobenzene.

20. A process as claimed in claim 1 wherein step (c) is conducted by using an excess of benzene as the solvent.

21. 5-(3,4-Dichlorophenyl)-dihydro-2(3H)-furanone.

22. 4-(3,4-Dichlorophenyl)-4-hydroxybutanoic acid or an alkali metal or amine addition salt thereof.

* * * * *